(12) United States Patent
Beimler et al.

(10) Patent No.: US 7,764,767 B2
(45) Date of Patent: Jul. 27, 2010

(54) DEVICE AND METHOD FOR ADJUSTING A DIAGNOSTIC UNIT

(75) Inventors: Franz Beimler, Weiden (DE); Michael Griener, Kulmain (DE)

(73) Assignee: Siemens Aktiengesellschaft, Munich (DE)

( * ) Notice: Subject to any disclaimer, the term of this patent is extended or adjusted under 35 U.S.C. 154(b) by 175 days.

(21) Appl. No.: 12/024,422

(22) Filed: Feb. 1, 2008

(65) Prior Publication Data
US 2008/0192896 A1 Aug. 14, 2008

(30) Foreign Application Priority Data
Feb. 13, 2007 (DE) .................... 10 2007 007 121

(51) Int. Cl.
H05G 1/54 (2006.01)
H05G 1/02 (2006.01)

(52) U.S. Cl. .................... 378/117; 378/196; 378/197

(58) Field of Classification Search ................ 378/114, 378/115, 117, 195–197, 208, 209
See application file for complete search history.

(56) References Cited

U.S. PATENT DOCUMENTS

| 3,473,024 | A | * | 10/1969 | Feiertag | 5/601 |
| 3,822,875 | A | * | 7/1974 | Schmedemann | 5/601 |
| 4,144,455 | A | * | 3/1979 | Lutz et al. | 5/601 |
| 5,762,608 | A | * | 6/1998 | Warne et al. | 600/425 |
| 6,272,368 | B1 | * | 8/2001 | Alexandrescu | 600/407 |
| 6,430,259 | B2 | * | 8/2002 | Meek et al. | 378/117 |
| 7,486,767 | B2 | * | 2/2009 | Sonobe et al. | 378/39 |
| 7,609,813 | B2 | * | 10/2009 | Curtis | 378/91 |
| 7,677,799 | B2 | * | 3/2010 | Jensen et al. | 378/205 |
| 2008/0119714 | A1 | * | 5/2008 | Meissner et al. | 600/407 |

FOREIGN PATENT DOCUMENTS

| DE | 689 19 801 T2 | 7/1994 |
| DE | 10 2005 018 326 A1 | 2/2006 |
| EP | 0 365 681 B1 | 7/1989 |
| WO | WO 2005/064281 A1 | 7/2005 |

OTHER PUBLICATIONS

German Office action dated Oct. 10, 2007 with an English translation.

* cited by examiner

*Primary Examiner*—Edward J Glick
*Assistant Examiner*—Thomas R Artman
(74) *Attorney, Agent, or Firm*—Brinks, Hofer, Gilson & Lione

(57) ABSTRACT

A diagnosis device, in particular an x-ray device, includes a patient couch which is rotatably mounted on a carrier device as well as a diagnosis unit, which is likewise mounted on the carrier device and can be moved along a longitudinal direction in parallel to the patient couch by a motor drive and an adjustment mechanism. A measuring device for measuring a measurement signal of a measured variable correlated with the drive force is provided in order to promptly identify a collision between the diagnosis unit and a patient mounted on the patient couch. A control unit is provided to evaluate the measurement signal. The control unit is designed in order to trigger a reaction when a predetermined value in respect of the measurement signal is exceeded.

16 Claims, 3 Drawing Sheets

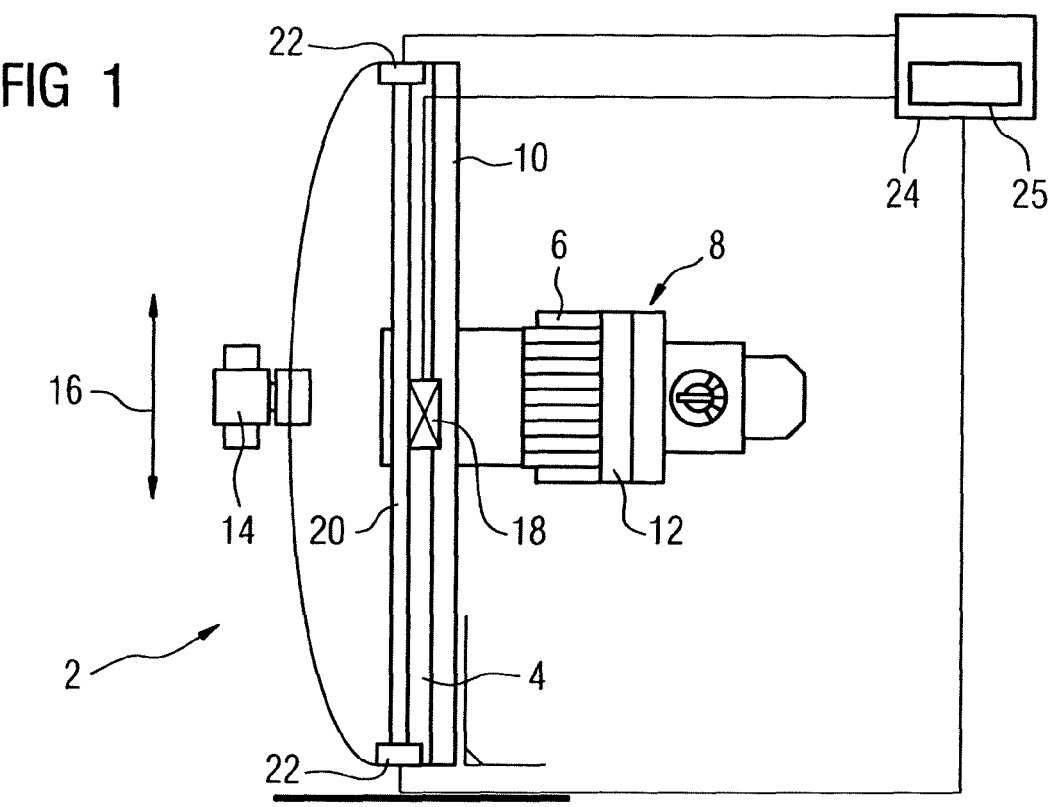
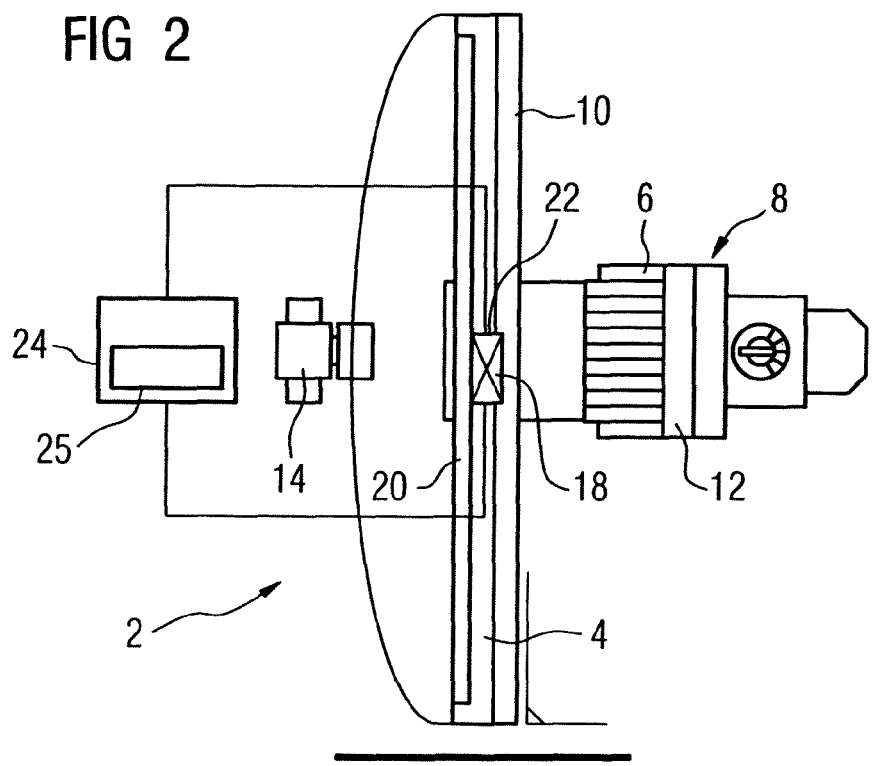

DEVICE AND METHOD FOR ADJUSTING A DIAGNOSTIC UNIT

The present patent document claims the benefit of German patent application DE 10 2007 007 121.5, filed Feb. 13, 2007, which is hereby incorporated by reference.

BACKGROUND

The present embodiments relate to a diagnosis device, such as an x-ray device. The diagnosis device includes a patient couch which is rotatably mounted on a carrier device, as well as a diagnosis unit, which is similarly mounted on the carrier device and can be moved along a longitudinal direction in parallel to the patient couch by a mechanical drive and an adjustment mechanism. The present embodiments also relate to a method for adjusting a diagnosis unit of a diagnosis device mounted on a carrier device, by a mechanical drive and an adjustment mechanism, along a longitudinal direction in parallel to a patient couch, which is likewise rotatably mounted on the carrier device.

Diagnosis devices, such as x-ray fluoroscopy devices, are frequently used to examine patients. An image receiver and an x-ray emitter are arranged above the patient and below the patient couch respectively. Such devices are usually referred to as undercouch devices. The AXIOM Sirescop SD fluoroscopy system by Siemens is an example of an undercouch device, which is suited to use in nearly all digital radiological and fluoroscopic methods. The said undercouch device includes a patient couch which is rotatably and/or pivotably mounted to a carrier device. It is possible to adjust said patient couch starting from a horizontal position if necessary about +/−90° into a vertical position, as a function of the examination to be carried out. During operation of the device, the image detector is moved as close as possible to the organ or tissue of the patient to be examined, in order to obtain high-quality recordings. The overall diagnosis unit, which includes the image detector and the x-ray emitter above and below the patient couch respectively, is thus moved along the patient couch supported by a holding device. In this process, the diagnosis unit moves independently of the alignment and inclination of the patient couch along a longitudinal direction of the patient couch in parallel with a reclining surface. The movement of the diagnosis unit in the longitudinal direction of the patient couch is controlled, for example, by a handle on the holding device. The handle is actuated manually. In order to enable the movement of the diagnosis unit in the differently inclined positions of the patient couch, a counterweight for balancing the weight of the diagnosis unit is provided. The counterweight is coupled to the diagnosis unit by an adjustment mechanism. With the adjustment mechanism, the counter weight is attached to the inside of the patient couch. The adjustment mechanism, which may include a friction wheel drive, aids the operator with moving the diagnosis unit. The weight of the diagnosis unit and the counter weight typically amount to several hundred kilograms in each instance, approximately 400 kg for example. The overall carrying mechanism and base construction are designed accordingly.

SUMMARY AND DESCRIPTION

The safety of the patient in an undercouch device is to be assured.

A diagnosis device, such as an x-ray device, include a patient couch which is rotatably mounted on a carrier device as well as a diagnosis unit, which is likewise mounted on the carrier device. The diagnosis unit may be moved along a longitudinal direction in parallel to the patient couch by a motor drive and an adjustment mechanism. A measuring device measures a measurement signal of a measured variable, which is correlated to the drive force exerted by the motor drive being provided. A control unit evaluates the measurement signal and is designed to trigger a reaction when a predetermined value in respect of the measurement signal is exceeded.

Safe operation of the diagnosis device which is gentle for the patient exists. Measuring the forces generated by the drive in order to move the diagnosis unit during operation of the diagnosis device is used to promptly detect a possible collision between the diagnosis unit and the patient. Both the measurement of the drive forces and also the detection of a collision are carried out, for example, completely automatically with the aid of a computer-aided system, so that the procedure is characterized by its efficiency and its high level of automation.

The drive force can either be measured directly or also indirectly by a measured variable correlated therewith. The temporal course of the drive force is detected and evaluated when the diagnosis unit is adjusted over the patient couch. Irregularities in the course, for instance a steep increase in the drive force, are interpreted as an impact between the diagnosis unit and the patient. Such an increase in the drive force points in particular to a collision if the measured drive force exceeds a predetermined device-specific value. The range of the measured drive forces depends both on the type of measuring device as well as on the dead weight of the diagnosis unit and the movement mechanism coupled therewith. Collision forces in the range of 100 N and less may be detected.

If an irregularity is detected in the course of the forces currently generated by the drive and/or affecting the adjustment mechanism, the x-ray unit is stopped, in one embodiment, as a reaction and in particular to cause the diagnosis unit to reverse. This prevents the diagnosis unit from being moved toward the patient with an increased drive force, which could result in the patient being injured.

In another embodiment, the control unit compares the measurement signal with the predetermined signal response. The detected measured variable, which specifies a current course of the drive force, is compared with an existing device-specific signal response. The present signal response is obtained for instance during a calibration process of the diagnosis device and represents the course of the drive force, if the diagnosis unit is moved unobstructed over the entire length of the patient couch.

The control unit may effect the reaction when a tolerance range, which is defined in respect of the predetermined signal response, is exceeded. As a result of the mostly discontinuous course of both the calibration curve and also the measurement curve of the drive force, a direct comparison of the currently measured signal response with the predetermined signal response is difficult. In order nevertheless to be able to reliably detect a collision, a tolerance range is defined on the basis of the predetermined calibration course. In this way, fluctuations in the currently measured signal response are not interpreted as a collision with the patient, provided the fluctuations lie within the tolerance range. This is only interpreted as a collision if a force is first measured when the diagnosis unit is moved along the patient couch, where the force exceeds this tolerance range, and the control unit effects a stop and in particular triggers the diagnosis device to reverse in the opposite direction in order to prevent the forces exerted on the patient by the diagnosis unit from increasing.

A storage device is expediently provided, in which a number of signal responses are stored for different positions of the patient couch or are calculated dynamically as a function of the position of the patient couch. The signal response of the drive force, which is necessary in order to move the diagnosis unit along the patient couch, is different for the differently inclined positions of the patient couch, as a function of the inclination angle of the patient couch during the examination. The different signal responses are determined and stored for the entire swivel range of the patient couch for all inclined positions of the patient couch, which differ by a defined angle of 1° for example, and/or can be calculated from known calibration values. During the examination of the patient at a later point in time, a suitable comparison course is thus available. A calibration of the device need not be carried out prior to each examination but the previously obtained calibration data record can instead be subsequently used at any time for comparison purposes. Alternatively, a dynamic calculation of the signal response can also be carried out as a function of the inclination angle of the patient couch. In this way, a tolerance range for the signal response can also be fixedly preset or preset as a function of the inclination angle of the patient couch.

The adjustment mechanism may be integrated in the patient couch. On the one hand, the overall diagnosis device requires less space and on the other hand the adjustment mechanism is itself protected against mechanical interferences during transportation and operation of the device.

The signal response of the drive force can be determined highly accurately by the measuring device designed for a direct force measurement of the drive force acting on the adjustment unit. The measuring device is designed in the manner of a force sensor or load cell with a spring element. Compressive and also tractive forces can be measured using such force sensors. The deformation of the spring element is converted into electrical voltage by way of strain gauges. The voltage is registered and calculated into a measured force value. Other measuring principles may be used. The developing tractive and compressive forces can thus also be measured in a contact-free fashion on the basis of the magnetostrictive effect by a sensor designed according to PCME technology. PCME stands here for "Pulse Current Modulated Encoding". The measuring principle of a sensor of this type is described in WO2005/064281.

According to an alternative embodiment, the measuring device is designed for a torque measurement. The torque of the drive is measured on the drive side, for instance on a shaft, which transfers the torque from one gear of the drive into the adjustment mechanism.

The drive forces may be recorded in a particularly simple fashion by designing the measuring device so as to measure a motor characteristic of the drive. For instance, the measuring device is designed to measure a motor current, a rotational speed, or a torque of the motor. The measured variable is correlated with the force generated on the drive side, so that the measurement signal may be converted easily and quickly by way of a suitable software in order to illustrate the force characteristic.

The torques developing in the drive and/or forces in the adjustment mechanism may be recorded at different points. In accordance with one embodiment, the measuring device is arranged between the drive and the adjustment mechanism. For example, the drive torque of the drive is detected by installing a torque sensor between a gear and the adjustment mechanism. With this variant, numerous embodiments of a torque sensor can be used; conventional torque sensors based on strain gauges or sensors provide contact-free measurement of the torque. Alternatively, a torsion sensor may be integrated as a force sensor in the drive axle, so that information relating to the forces acting on the adjustment mechanism are obtained by the measured torsion in the drive axle.

According to an alternative embodiment, the measuring device is coupled to a bearing of the adjustment mechanism. The measuring device is embodied in the manner of a force sensor, e.g. a sensor in bending beam design, which is characterized by its simple design, low price and high accuracy. Such a force sensor is fixedly mounted on the patient couch with one end and is coupled to the adjustment mechanism with its other end, so that the adjustment mechanism is mounted within the patient couch in a floating manner thereover. The force sensor(s) is/are directly mounted on the patient couch, so that the friction losses from the motor, gear and the adjustment mechanism are not recorded therewith.

In accordance with a further embodiment, the measuring device is arranged between the adjustment mechanism and the diagnosis unit, such as between the holding device for the diagnosis unit. The measuring device is arranged directly between the drive chain and the holding device for the diagnosis unit. An arrangement of the measuring device of this type may be used when the drive is not coupled to the holding device but is instead fixedly mounted on another position in the patient couch.

Advantageously, the total mass of the diagnosis device is significantly reduced by comparison with conventional diagnosis devices with a counterweight, in particular by a third, which advantageously affects the transportation costs and requirements placed on the composition of the ground at the installation location. With the suggested diagnosis device, the counterweight hitherto used with undercouch devices is replaced by the fixedly coupled drive in combination with the measuring device for safety monitoring purposes, as a result of which the safety of the patient is significantly improved in respect of possible collisions with the diagnosis unit.

A method is provided for adjusting a diagnosis unit of a diagnosis device mounted on a carrier device along a longitudinal direction in parallel with the patient couch by a motor drive and an adjustment mechanism. The patient couch likewise is mounted in a rotatable fashion on the carrier device. A measurement signal of a measured variable is correlated with the drive force exerted by the motor drive being measured by a measuring device, and the measured signal is evaluated with the aid of a control unit. A reaction is triggered by the control unit when a predetermined value in respect of the measurement signal is exceeded.

The course of the drive forces may change over time as a result of the ageing and wear of the adjustment mechanism as well as the mechanical components of the drive. In order that a current calibration course exists by comparison with the values measured during an examination, signal responses are used for the evaluation. The signal responses may be updated at specific time intervals during the course of the operation of the diagnosis device. To this end, calibration runs may be implemented from time to time with the respective diagnosis device itself. Alternatively, typical empirical signal responses may also be stored for instance as reference curves, as a function of the age or the hours of operation.

BRIEF DESCRIPTION OF THE DRAWINGS

FIG. 1 shows a schematic illustration of one embodiment of a longitudinal section of a diagnosis device with a patient couch in the vertical position and with two force sensors arranged in the bearing points of an adjustment mechanism of the device;

FIG. 2 shows a schematic illustration of one embodiment of a longitudinal section of a diagnosis device with a patient couch in a vertical position and with a force sensor coupled to a drive of the device;

Identical reference characters have the same meaning in the different figures.

DETAILED DESCRIPTION

Figure 3:
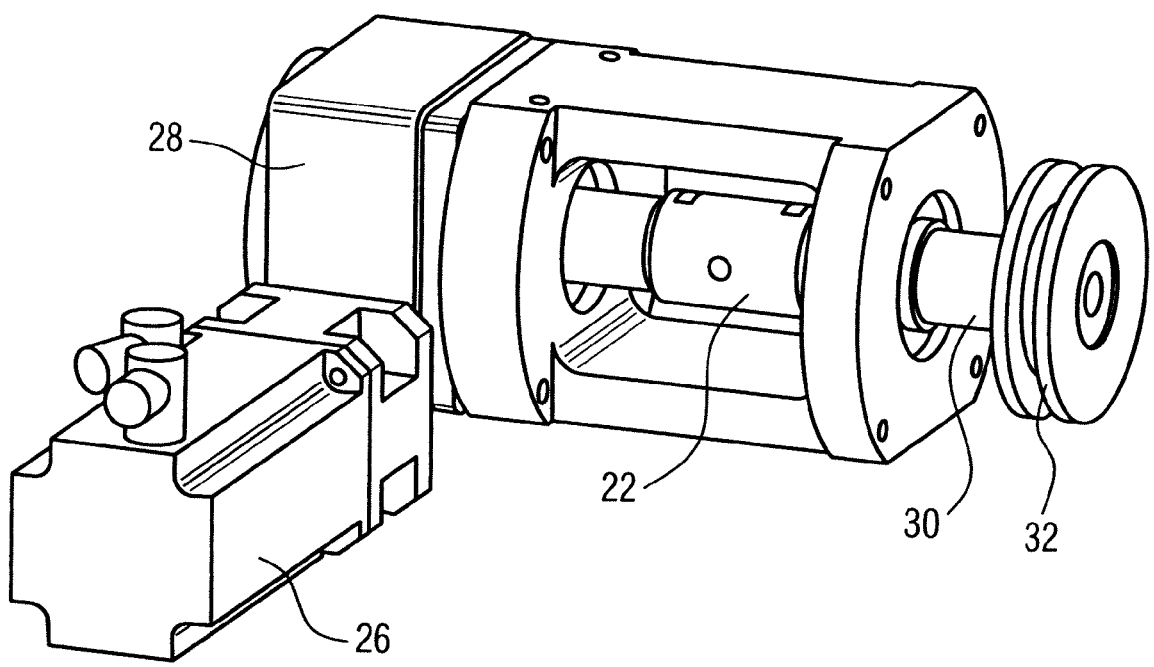
FIG. 3 shows a schematic illustration of one embodiment of a perspective view of a drive as shown in FIG. 2.

FIG. 1 shows a diagnosis device 2, which is provided for x-ray examinations. The diagnosis device 2 includes a trough-shaped patient couch 4, which is shown in a vertical position inclined by +90°, as well as a holding device 6 for a diagnosis unit 8. The diagnosis unit 8 is an x-ray detector 12 arranged over a reclining surface 10 of the patient couch 4 and an x-ray emitter 14 mechanically coupled hereto. The x-ray emitter 14 is arranged opposite to the x-ray detector 12 and is located below the patient couch 4 when the patient couch 4 is in a horizontal position.

The patient couch 4 and the holding device 6 are arranged in a pivotable fashion on a carrier device (not shown here) such that the patient couch 4 is able to carry out a rotation by +/−90° starting from a horizontal position about a point of rotation (not shown here) located approximately in the center of the holding device 6 according to FIG. 1. With the rotation of the couch 4, the holding device 6 is rotated together with the diagnosis unit 8 so that the diagnosis unit 8 always has the same orientation in respect of the table 4. The conventional position essentially corresponds to a view on the illustration according to FIG. 1 from the left side.

During operation of the device 2, the diagnosis unit 8 is moved along a longitudinal direction 16 of the patient couch 4 in parallel to the reclining surface 10. In order to adjust the diagnosis unit 8 in the longitudinal direction 16, a drive 18 installed in this exemplary embodiment in the holding device 6 is provided. The drive 18 moves the entire holding device 6 along an adjustment axle 20 which is arranged within the trough-shaped patient couch 4 and extends in the longitudinal direction 16. The adjustment axle 20 forms an adjustment mechanism.

To promptly identify an impact between the diagnosis unit 8 and a patient mounted on the patient couch 4 (not shown here), two measuring devices 22 are arranged on both ends of the adjustment axle 20 in the region of the adjustment axle's 20 bearing on the patient couch 4. The measuring devices are embodied in the manner of a force sensor and include a spring element (not shown in further detail). The force sensors 22 are fixedly connected on one end to the patient couch 4 and are coupled to the adjustment axle 20 on the other end. Both force sensors thus essentially form the bearing of the adjustment axle 20 in the patient couch 4. The adjustment axle 20 is mounted in a floating fashion over the force sensors 22 so that the spring elements of the force sensors 22 are able to compress or expand under the influence of drive forces.

The force sensors 22 measure the force transferred from the drive 18 into the adjustment axle 20. The measurement data is transmitted to a control unit 24 with a storage device 25. The control unit 24 evaluates the data and converts the data to or uses the data as a force characteristic. (see FIG. 5). When detecting a collision, the control unit 24 controls the drive 18 in order to stop and triggers a movement of the holding device 6 in the opposite direction, in order to break the contact between the diagnosis unit 8 and the patient. Identifying a collision and correspondingly reversing the diagnosis unit 8 is thus carried out completely automatically.

An alternative embodiment of the measuring device 22 is shown in FIG. 2. The measuring device 22 is arranged between the drive 18 and the adjustment mechanism 20 and detects the drive torque generated by a motor 26 of the drive 18 and transmitted to the adjustment mechanism 22 by way of a gear 28, as shown in FIG. 3. In this way, the measuring device 22 is embodied in the manner of a torque sensor and is arranged in this exemplary embodiment on a drive shaft 30 between the gear 28 and a chain wheel 32 of the adjustment mechanism 22. As the drive torque is correlated with the force produced by the drive 18 in order to adjust the diagnosis unit 8, the measurement signal received by the control unit 24 is simply converted into a drive force and is, if necessary, shown.

Figure 4:
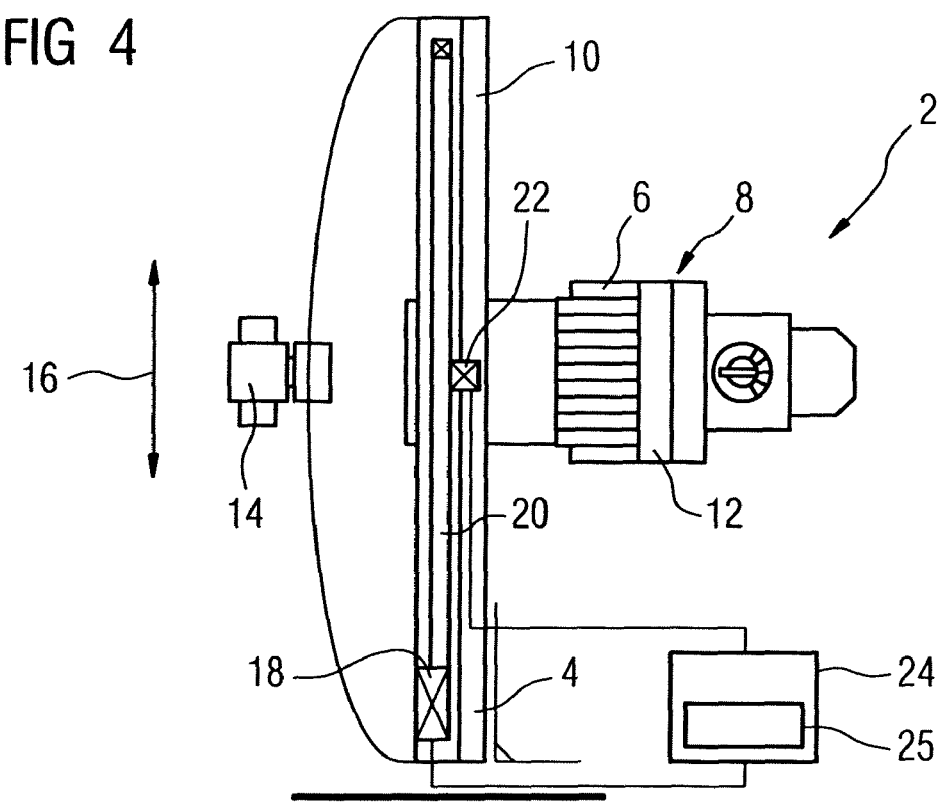
FIG. 4 shows a schematic illustration of one embodiment of a longitudinal section of a diagnosis device with a patient couch in the vertical position and with a force sensor arranged between an adjustment mechanism and a bearing of a diagnosis unit.

A further exemplary embodiment for a diagnosis device 2 is shown in FIG. 4. The drive force, which affects the adjustment mechanism 20 when the holding device 6 is moved, is measured and evaluated in order to detect a collision. The drive 18 is not installed in the holding device 6, but is instead fixed to the patient couch 4 in the region of a bearing point of the adjustment mechanism 20. In this exemplary embodiment, the adjustment mechanism 20 is embodied in the manner of a chain drive. The holding device 6 is fixedly connected to the adjustment mechanism 20 so that the holding device 6 is also moved when the adjustment mechanism 20 is adjusted by way of the drive 18 and a movement is implemented in the longitudinal direction 16. The measuring device 22 is likewise a force sensor, which is arranged between the holding device 6 and the adjustment mechanism 20.

Alternatively to the force sensor 22, the measuring device 22 may be a torque sensor, in accordance with FIG. 4, as was described in conjunction with FIG. 2 and FIG. 3, or also a torsion sensor, which is attached directly to the drive 18.

The drive force may be determined by measuring a characteristic value of the motor 26, in particular by measuring the motor current. The motor current monitoring represents the simplest possibility of recording the torque of the drive 18. Minimum accuracy is however to be expected.

Figure 5:
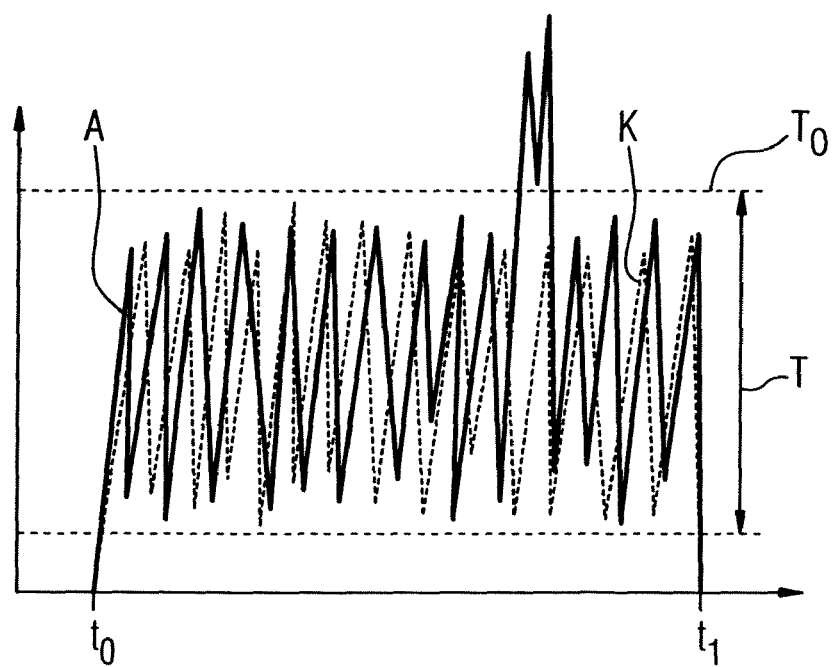
FIG. 5 shows a schematic illustration of one embodiment of a diagram qualitatively indicating the courses of the drive forces developing during normal operation and in the event of a collision during an examination with a diagnosis device in a horizontal device position of 0°.

The course of the measured drive forces over time for a horizontal device position at 0° is shown qualitatively in FIG. 5. A predetermined signal response k stored in the storage device 25 of the control unit 24 is used. The response k is recorded and stored at an earlier point in time with a calibration process without a patient on the patient couch 4. The calibration signal response K is used as a basis for the comparison. The response k specifies a region where the signal of the drive forces fluctuates between two time points $t_0$ and $t_1$, when the diagnosis unit 8 is moved along the patient couch 4, without interferences herewith existing as a result of a collision with a patient. A tolerance range T is defined on the basis of the calibration signal response K, within which tolerance range is located the normal course of the drive forces.

During operation of the diagnosis device 2, the control unit 24 monitors whether the currently measured measurement signal A and/or the drive forces determined are located within the tolerance range T or exceed an upper limit $T_0$ of the tolerance range T. For this purpose, the currently determined drive forces are in particular jointly visualized in a diagram with the predetermined signal response K and the tolerance range T. A peak in the measurement signal A exceeding the upper limit $T_0$ of the tolerance range T is interpreted by the control unit 24 as a collision of the diagnosis unit 8 with the patient. Detection of the peak or exceeding the tolerance range promptly triggers the diagnosis unit 8 to reverse.

The normal course of the drive force is on the one hand device-specific and on the other hand depends on the inclination of the patient couch 4 of the holding device 6. The forces which have to be surmounted in order to move the holding device can be specified as a function of the mass of the holding device 6, the adjustment unit 20 and the drive, multiplied by the sine of the inclination angle of the patient couch 4. Calibration signal responses are thus determined and stored for many device positions or are calculated from device data. In particular, the signal responses K are registered and calculated for all device positions with a difference of 1° for instance.

If the device 2 is subjected to wear and ageing processes during operation, an ever larger drive force is needed over time in order to move the holding device 6 and also in the event of a collision. Provision is made in this case for the calibration signal response K to be reproduced for each device position during operation of the device 2 a number of times, in order to always supply a current tolerance range T for the evaluation of the measurement data.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A diagnosis device comprises:
    a patient couch mounted in a rotatable fashion on a carrier device;
    a diagnosis unit mounted on the carrier device and operable to be moved along a longitudinal direction in parallel to the patient couch;
    a motor drive and an adjustment mechanism operable to move the diagnosis unit;
    a measuring device operable to measure a measurement signal of a measured variable correlated with the drive force exerted by the motor drive; and
    a control unit operable to evaluate the measurement signal, the control unit operable to trigger a reaction when a predetermined value in respect of the measurement signal is exceeded,
    wherein the diagnosis unit is mounted in a weight-free fashion and wherein the control unit controls the motor drive in combination with the measuring device to prevent collision between patient and the diagnosis unit.

2. The diagnosis device as claimed in claim 1, wherein the control unit is operable to stop a further movement of the diagnosis unit and is operable to cause the diagnosis unit to reverse.

3. The diagnosis device as claimed in claim 1, wherein the control unit is operable to compare the measurement signal with a predetermined signal response.

4. The diagnosis device as claimed in claim 3, wherein the control unit is operable to effect the reaction when a tolerance range defined in respect of the predetermined signal response is exceeded.

5. The diagnosis device as claimed in claim 4, further comprising:
    a storage device operable to store a number of signal responses for different positions of the patient couch.

6. The diagnosis device as claimed in claim 1, wherein the adjustment mechanism is installed in the patient couch.

7. The diagnosis device as claimed claim 1, wherein the measuring device is operable for direct force measurement.

8. The diagnosis device as claimed in claim 1, wherein the measuring device is operable for a torque measurement.

9. The diagnosis device as claimed in claim 1, wherein the measuring device is operable to measure a motor characteristic of the drive.

10. The diagnosis device as claimed in claim 1, wherein the measuring device is arranged between the drive and the adjustment mechanism.

11. The diagnosis device as claimed in claim 1, wherein the measuring device is coupled to a bearing of the adjustment mechanism.

12. The diagnosis device as claimed in claim 1, wherein the measuring device is arranged between the diagnosis unit and the adjustment mechanism.

13. The diagnosis device as claimed in claim 1 wherein the diagnosis device comprises an x-ray device.

14. A method for adjusting a diagnosis unit of a diagnosis device mounted on a carrier device along a longitudinal direction in parallel to a patient couch, the patient couch being rotatably mounted on the carrier device, the method comprising:
    moving the diagnosis unit with a motor drive and an adjustment mechanism;
    measuring a measurement signal of a measured variable correlated with a drive force exerted by the motor drive, the measuring being performed by a measuring device;
    evaluating, with a control unit, the measurement signal; and
    triggering a reaction by the control unit when a predetermined value is exceeded by the measurement signal.
    wherein the diagnosis unit is mounted in a weight-free fashion and further controlling the motor drive in combination with the measuring device to prevent collision between patient and the diagnosis unit.

15. The method as claimed in claim 14, further comprising:
    updating stored signal responses (K) of the measured variable in the course of the operation during the evaluation.

16. The diagnosis device as claimed in claim 14, further comprising:
    a storage device operable to calculate a number of signal responses for different positions of the patient couch.

* * * * *